United States Patent
Mei et al.

(10) Patent No.: US 10,605,711 B2
(45) Date of Patent: Mar. 31, 2020

(54) ULTRASONIC MEASURING METHOD AND SYSTEM FOR MEASURING PARTICLE SIZE AND MASS CONCENTRATION

(71) Applicants: GENERAL ELECTRIC COMPANY, Schenectady, NY (US); Yan Mei, Shanghai (CN); Longtao Yuan, Shanghai (CN); Ran Niu, Shanghai (CN); Weihua Shang, Shanghai (CN); Jing Ye, Shanghai (CN); Xin Qu, Shanghai (CN)

(72) Inventors: Yan Mei, Shanghai (CN); Longtao Yuan, Shanghai (CN); Ran Niu, Shanghai (CN); Weihua Shang, Shanghai (CN); Jing Ye, Shanghai (CN); Xin Qu, Shanghai (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/535,278

(22) PCT Filed: Dec. 11, 2015

(86) PCT No.: PCT/CN2015/097128
§ 371 (c)(1),
(2) Date: Oct. 30, 2017

(87) PCT Pub. No.: WO2016/091208
PCT Pub. Date: Jun. 16, 2016

(65) Prior Publication Data
US 2018/0088017 A1 Mar. 29, 2018

(30) Foreign Application Priority Data
Dec. 12, 2014 (CN) .......................... 2014 1 0769173

(51) Int. Cl.
*G01N 15/02* (2006.01)
*G01N 15/06* (2006.01)
(Continued)

(52) U.S. Cl.
CPC ............. *G01N 15/02* (2013.01); *G01N 15/06* (2013.01); *G01N 29/032* (2013.01); *G01N 29/11* (2013.01);
(Continued)

(58) Field of Classification Search
CPC ....... G01N 2291/02416; G01N 29/032; G01N 15/02; G01N 15/0211; G01N 2015/003;
(Continued)

(56) References Cited

U.S. PATENT DOCUMENTS 4,412,451 A * 11/1983 Uusitalo .............. G01N 29/032
73/599
4,413,511 A 11/1983 Godbey
(Continued)

FOREIGN PATENT DOCUMENTS

CN 1934423 A 3/2007
CN 201096703 Y 8/2008
(Continued)

OTHER PUBLICATIONS

Marana, A.N., et al., "An Intelligent System for Petroleum Well Drilling Cutting Analysis," International Conference on Adaptive and Intelligent Systems, pp. 37-42 (2009).
(Continued)

*Primary Examiner* — David A Rogers
(74) *Attorney, Agent, or Firm* — Laura L. Pollander

(57) ABSTRACT

A measurement method comprising: transmitting a plurality of ultrasonic signals to the fluid to be measured; receiving an return signal reflected or scattered from the particles in the fluid under test; calculating a one or more calculated values of the R parameter associated with the particle properties based on the return signal; determining the theoretical curve of the R parameter associated with the particle properties; and determining the mean diameter of the particles in the
(Continued)

fluid based on the one or more calculated values of the R parameter and the theoretical curve of the R parameter; determining the mass concentration of the particles in the fluid according to the mean diameter of the particles. Embodiments also provide a measurement system for measuring the mean diameter and mass concentration of the particles.

10 Claims, 4 Drawing Sheets

(51) Int. Cl.
    *G01N 29/11* (2006.01)
    *G01N 29/44* (2006.01)
    *G01N 29/032* (2006.01)

(52) U.S. Cl.
    CPC . *G01N 29/449* (2013.01); *G01N 2291/02408* (2013.01); *G01N 2291/02809* (2013.01); *G01N 2291/044* (2013.01); *G01N 2291/101* (2013.01); *G01N 2291/106* (2013.01)

(58) Field of Classification Search
    CPC .............. G01N 2291/102; G01N 15/04; G01N 2291/015
    See application file for complete search history.

(56) References Cited

U.S. PATENT DOCUMENTS

| | | | |
|---|---|---|---|
| 5,777,231 A | 7/1998 | Patel et al. | |
| 6,119,510 A * | 9/2000 | Carasso | G01N 15/0205 356/437 |
| 6,176,323 B1 | 1/2001 | Weirich et al. | |
| 6,205,848 B1 | 3/2001 | Faber et al. | |
| 6,768,106 B2 | 7/2004 | Gzara et al. | |
| 7,331,233 B2 * | 2/2008 | Scott | G01N 15/02 73/596 |
| 7,353,709 B2 * | 4/2008 | Kruger | G01N 29/11 73/599 |
| 7,619,734 B2 * | 11/2009 | Chamberlin | G01J 3/10 356/335 |
| 7,719,682 B2 * | 5/2010 | Chamberlin | G01J 3/10 356/335 |
| 8,154,723 B2 * | 4/2012 | Fu | G01N 15/0205 356/335 |
| 8,286,466 B2 | 10/2012 | Gysling | |
| 8,942,928 B2 * | 1/2015 | Prakash | G01N 29/032 702/22 |
| 9,714,893 B2 * | 7/2017 | Driscoll | G01N 15/02 |
| 9,726,590 B2 * | 8/2017 | Hies | G01N 29/348 |
| 9,970,903 B1 * | 5/2018 | Gerardi | G01N 29/032 |
| 2009/0032304 A1 | 2/2009 | Groh | |
| 2009/0145661 A1 | 6/2009 | Jeffryes et al. | |
| 2011/0209540 A1 | 9/2011 | Banks et al. | |

FOREIGN PATENT DOCUMENTS

| | | |
|---|---|---|
| CN | 102985816 A | 3/2013 |
| CN | 103983549 A | 8/2014 |
| JP | H4-95870 A | 3/1992 |
| JP | 2009-250702 A | 10/2009 |

OTHER PUBLICATIONS

International Search Report and Written Opinion issued in connection with corresponding PCT Application No. PCT/CN2015/097128 dated Mar. 1, 2016.

Machine Translation and First Office Action and Search issued in connection with corresponding CN Application No. 201410769173.X dated Jan. 17, 2018.

Office Action issued in connection with corresponding MX Application No. MX/A/2017/007579 dated Oct. 3, 2018.

* cited by examiner

ULTRASONIC MEASURING METHOD AND SYSTEM FOR MEASURING PARTICLE SIZE AND MASS CONCENTRATION

BACKGROUND

The present invention relates to a measurement method and system, and more particularly, to a method and system for measuring the mean diameter and mass concentration of suspended particles in a fluid.

In the method of measuring fluid flow using the Doppler principle, the particles suspended in the fluid reflect or scatter the ultrasonic signal transmitted by the one or more transducers. The energy of the Doppler return signal reflected or scattered is related to the diameter and mass concentration of the particles. When the diameter of the particles is small or the mass concentration is low, the return signal is weaker; when the diameter of the particles increases or the mass concentration increases, the return signal also becomes stronger. However, on the one hand, when the diameter of the particles is too large, due to their own weight being too heavy, the suspended particles have a larger velocity relative to the fluid itself, in this case, if the movement velocity of the suspended particles is still used as the movement velocity of the fluid itself, it will reduce the accuracy of the flow measurement; on the other hand, when the mass concentration of the particles is too large, the attenuation of the ultrasonic signal in the fluid is also larger, where the return signal received by the one or more transducers is also weaker, with even a lower signal-to-noise ratio affecting the measurement of flow rate. Therefore, it is particularly important to measure the diameter and mass concentration of the particles during the process of measuring the flow rate of a fluid using the Doppler principle.

BRIEF DESCRIPTION OF THE INVENTION

An aspect of the present invention provides a measurement method. The measurement method comprising: transmitting a plurality of ultrasonic signals to the fluid to be measured; receiving an return signal reflected or scattered from the particles in the fluid under test; calculating a one or more calculated values of the R parameter associated with the particle properties based on the return signal; determining the theoretical curve of the R parameter associated with the particle properties; and determining the mean diameter of the particles in the fluid based on the one or more calculated values of the R parameter and the theoretical curve of the R parameter; determining the mass concentration of the particles in the fluid according to the mean diameter of the particles.

Another aspect of the present invention provides a measurement system. The measurement system comprises: one or more transducers configured to transmit a plurality of ultrasonic signals to the fluid being measured and receive a plurality of return signals reflected or scattered from the particles; and a processor, coupled to the one or more transducers, and configured to calculate one or more calculated values of a R parameter related to particle properties of the particles according to the plurality of return signals, determine a theoretical curve of the R parameter related to the particle properties, determine a mean diameter of the particles according to the one or more calculated values and the theoretical curve of the R parameter, and determine a mass concentration of the particles according the mean diameter.

BRIEF DESCRIPTION OF THE DRAWINGS

The present invention will be better understood from the following description of embodiments of the present invention taken in conjunction with the accompanying drawings, in which.

DETAILED DESCRIPTION OF THE INVENTION

Unless otherwise defined, the technical and scientific terms used in the claims and the specification are as they are usually understood by those skilled in the art to which the present invention pertains. "First", "second" and similar words used in this specification and in the claims do not denote any order, quantity or importance, but are merely intended to distinguish between different constituents. Similarly, the terms "one", "a" and the like are not meant to be limiting, but rather denote the presence of at least one. Unless otherwise indicated, "front", "rear", "lower part" and/or "upper part" as well as similar terms are used for ease of illustration only, and are not limited to one location or a spatial orientation. In addition, "connected", "coupled" and similar words are not used to distinguish between direct or indirect connections between two elements. Of course, such elements may be connected directly or indirectly, unless otherwise stated.

Figure 1:
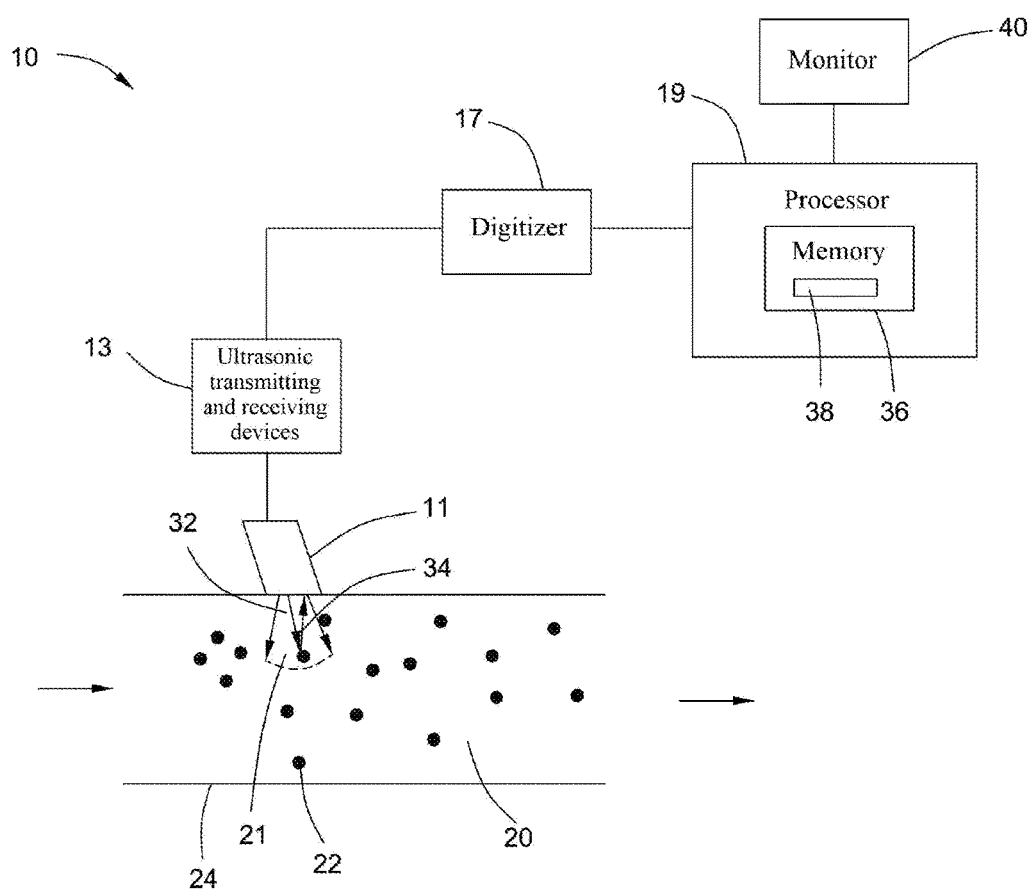
FIG. 1 shows a schematic view of one embodiment of the measurement system.

FIG. 1 shows a schematic view of a measurement system 10 of one embodiment. The measurement system 10 may be used to measure the size and mass concentration of the particles in the fluid 20. The fluid 20 may flow inside the conduit 24 along the direction of the arrows in the Figure. Particles 22 are suspended within the fluid 20, for example, impurities and contaminants such as debris, bubbles, mud, and so on. The shape, size and distribution of the particles 22 are generally uncertain, and are often varied depending on the environment of actual application. In a typical application, the measurement system 10 may be used in petroleum or natural gas drilling wells to measure the particle size and concentration of the liquid flowing back during the drilling process, which is often suspended with rocks, mud and other impurities generated by the drilling wells. However, the measurement system 10 is not limited to this field of application and may be applied to other fields.

The measurement system 10 comprises one or more ultrasonic transducers 11, one or more ultrasonic transmitting and receiving devices 13, a digitizer 17 and a processor 19. The one or more ultrasonic transducers 11 can be mounted on the walls of the conduit 24. The one or more ultrasonic transmitting and receiving devices 13 generate and transmit electrical signals to the one or more ultrasonic transducers 11. The one or more ultrasonic transducers 11 convert the electrical signals into ultrasonic signals (ultrasonic waves) 32, which is transmitted to the fluid 20. The ultrasonic signals transmitted by the one or more ultrasonic transducers 11 may cover a plurality of regions in the fluid 20. An ultrasonic signal transmitted by an ultrasonic transducer 11 may cover a region 21 that approximate a cone. The one or more ultrasonic transducers 11 generally comprises piezoelectric elements capable of converting an electrical signal into a physical pulse (ultrasonic signal 32 for the present embodiment), and the frequency of the ultrasonic signal 32 is being controlled by the frequency of the electrical signal. In the present embodiment, the one or more ultrasonic transducers 11 transmit ultrasonic signals 32 having different frequencies ($f_1, f_2, \ldots f_n$) to the fluid 20. In another embodiment, the one or more ultrasonic transducers 11 transmit ultrasonic signals 32 of a single frequency to the fluid 20. Only one ultrasonic transducer 11 is shown in FIG. 1. In some embodiments, a plurality of ultrasonic transducers 11 may be used to transmit ultrasonic signals.

The ultrasonic signals 32 may be reflected or scattered back by the particles 22. At least some of the return signals 34 reflected or scattered by the particles 22 of the fluid 20 are received by the one or more ultrasonic transducers 11. The one or more ultrasonic transducers 11 convert the return signals 34 into electrical signals. The one or more ultrasonic transmitting and receiving devices 13 receives the electrical signals output from the one or more ultrasonic transducers 11 and amplify the amplitude of the electrical signals. The digitizer 17 converts the electrical signals amplified by the one or more ultrasonic transmitting and receiving devices 13 into digital signals for the processor 19.

The processor 19 comprises program instructions encoded in the fixed memory 36 or the removable memory 38, to generate the mean diameter of the particles and/or the mass concentration of the particles by processing the digital signals from the digitizer 17. In some embodiments, the processor 19 is also used to generate the flow rate, discharge, etc. of the fluid 20. In one embodiment, the processor 19 is a microcomputer that comprises a central processing unit (CPU), read only memory (ROM), random access memory (RAM), and so on. The processor 19 is connected to the display 40 to output information of the fluid 20 such as particle size, particle mass concentration and so on.

Figure 2:
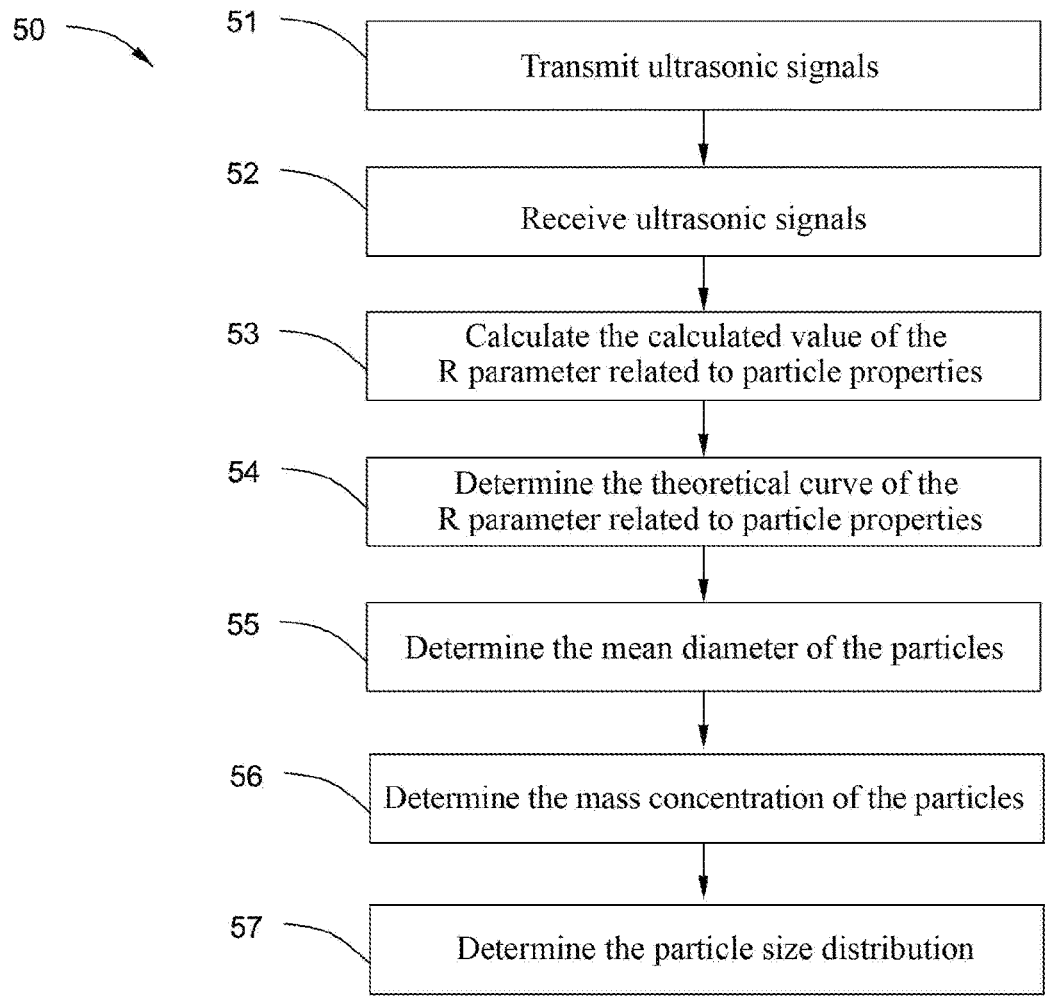
FIG. 2 shows a flow chart of one embodiment of the measurement method.

FIG. 2 shows a flow chart of a measurement method 50 of one embodiment. The measurement method 50 may be used to measure the mean diameter and mass concentration of the particles in the fluid. The measurement method 50 may be implemented by using the measurement system 10 shown in FIG. 1, but is not limited thereto. In Step 51, ultrasonic signals are transmitted to the fluid. The ultrasonic signals may be transmitted through the one or more ultrasonic transducers to at least on region of the fluid. The ultrasonic signals transmitted by an ultrasonic transducer can cover a region that approximate a cone. A plurality of ultrasonic transducers may transmit ultrasonic signals to a plurality of regions that approximate a cone in the fluid. In one embodiment, ultrasonic signals of a single frequency are transmitted. In another embodiment, ultrasonic signals having different frequencies ($f_1, f_2, \ldots f_n$) are transmitted. The frequencies of the ultrasonic signals can be adjusted according to the particle size being measured, with the ultrasonic signals having low frequencies used to measure larger particles, and the ultrasonic signals having high frequencies used to measure smaller particles.

In step 52, the return signals reflected or scattered from the particles in the fluid are received. The ultrasonic signals transmitted in step 51 are transmitted to the particles in the fluid, reflected or scattered by the particles, at least part of the reflected or scattered return signals arrives at the one or more ultrasonic transducers, and is received by the one or more ultrasonic transducers. The return signals is converted into electrical signals, as well as amplified and converted into digital signals for processing.

In step 53, the calculated value of the R parameter related to the particle properties is calculated from the return signals. The particle properties include size, distribution, density and reflectance of the particles within regions covered by the one or more ultrasonic transducers, excluding the concentration of the particles. The R parameter is independent of the particle concentration. At least one R parameter can be calculated in a region covered by the ultrasonic signals transmitted by an ultrasonic transducer. In one embodiment, the region covered by the ultrasonic signals transmitted by an ultrasonic transducer corresponds to an R parameter. In an embodiment, a region covered by ultrasonic signals may be further divided into a plurality of small regions, with an R parameter calculated for each small region. Step 53 for calculating the R parameter comprises determining the voltage amplitude mean square of the return signals as a function of the particle properties. In the present embodiment, the function is also related to the properties of the fluid, the properties of the transducer and the properties of the measurement system. Then, the calculated value of the R parameter is calculated based on the function. In the present embodiment, it is assumed that the particles are uniformly suspended in the fluid, and the return signals from each particles are not coherent. Using the RMS function of the return signals, the function is expressed as shown in the following equation (1):

$$V_{rms}(r) = \frac{K_s K_t}{r\psi} \sqrt{M}\, e^{-2r(\alpha_m + \alpha_s)} \tag{1}$$

Where $V_{rms}$ is the voltage amplitude mean square of the return signals. r is the distance from the transducer to the measured particle and can be obtained by the sampling time. $K_s$, M and $\alpha_s$ are parameters related to particle size and/or mass concentration. $K_s$ is a parameter that reflects the particle size, particle distribution, particle density, and particle scattering properties. M is the mass concentration of the particles. $\alpha_m$ and $\alpha_s$ are the attenuation coefficients, where $\alpha_m$ reflects the attenuation of the ultrasonic signals in the fluid and can be measured. $\alpha_s$ reflects the attenuation of the ultrasonic signals by the suspended particles in the fluid. In the application to drilling wells, $\alpha_m$ primarily reflects the attenuation caused by drilling mud on the ultrasonic signals, $\alpha_s$ reflects the attenuation caused by the suspended particles in the drilling mud on the ultrasonic signals. $K_t$ is a system constant related to the fixed properties of the measurement system and the ultrasonic transducer. $\Psi$ is the near field correction factor of the ultrasonic transducer and can be calculated according to the empirical formula. Further, $K_s$ can be calculated using the following expression (2):

$$K_s = \langle f \rangle / \sqrt{\langle a_s \rangle \rho_s} \tag{2}$$

Where $\langle f \rangle$ is the particles' average backscatter form function, which reflects the ability of the particles in the unit volume to backscatter the energy of the ultrasound, which is related to the size distribution of the particles. $\langle a_s \rangle$ is the average particle diameter. $\rho_s$ is the particle density.

$\alpha_s$ can be calculated using the following expression (3):

$$\alpha_s = 3M\langle \chi \rangle / 4\langle a_s \rangle \rho_s \tag{3}$$

Where $\langle x \rangle$ is the average normalized total scattering cross-section).

For the ultrasonic signals of one frequency (e.g. frequency $f_1$), the parameters $A = \sqrt{M}/\sqrt{\langle a_s \rangle \rho_s}$ and $B = \alpha_m + 3/4 A^2 \langle \chi \rangle$ are defined. According to the expressions (2) and (3) of the custom parameters A and B as well as $K_s$ and $\alpha_s$, function 1 is transformed into the following function (4):

$$V_{rms}(r) = \frac{A\langle f\rangle K_r}{r\psi}e^{-2rB} \quad (4)$$

The exponent −2rB can be calculated from the function (4), where the distance r from the particle to the transducer can be calculated by the sampling time, so that the parameter B can be calculated.

According to the expression of parameter B, the parameter $C_1=A\sqrt{\langle X\rangle}$ is further defined, and the value of parameter $C_1$ can be calculated according to the value of parameter B that has been calculated. Parameter $C_2=A\langle f\rangle$ is defined, and the value of $C_2$ is calculated based on the value of parameter B and function (4). Parameter $R=C_2/C_1$ is defined, and the calculated value of parameter R can be calculated using the values of $C_1$ and $C_2$. Also, according to the expressions of $C_1$ and $C_2$, another formula to calculate parameter $R=\langle f\rangle/\sqrt{\langle\chi\rangle}$ can be obtained, it can be seen from the formula to calculate parameter R, that parameter R is related to $\langle f\rangle$ and $\langle x\rangle$. While $\langle f\rangle$ and $\langle x\rangle$ are related to particle size distribution, particle and fluid density, as well as particle and fluid elasticity. In the present embodiment, it is assumed that the distribution of the particles is a Gaussian distribution, and it is further assumed that the variance of the particle diameters in the Gaussian distribution is known. Assuming that the density and elasticity of the particles and the fluid are known, the R parameter changes with changes in mean diameter of the particles, which does not reflect particle concentration. In other embodiments, it may be assumed that the particles are distributed in other forms. The variance of particle diameters can be set according to empirical values, while the density and elasticity of the particles and the fluid can be obtained through experiments, etc. Therefore, only the parameters related to the mean diameter of the particles are isolated for subsequent calculations. In one embodiment, for each of the different ultrasonic frequencies $f_1$-$f_n$, the calculated values $R_1$-$R_n$ of the R parameter under the corresponding frequencies can be calculated according to the method mentioned above.

In step 54, a theoretical curve of the R parameter related to the particle properties is determined. The theoretical curve of the R parameter relative to the mean diameter of the particles can be calculated according to the formula $\langle f\rangle/\sqrt{\langle\chi\rangle}$. In one embodiment, the theoretical curve for obtaining the R parameters at different frequencies $f_1$-$f_n$ can be calculated. In one embodiment, the theoretical value $R_{theoretical,i}$ of the R parameter may be calculated in advance and stored in the memory 36, 38 of the processor 19 as shown in FIG. 1.

Figure 3:
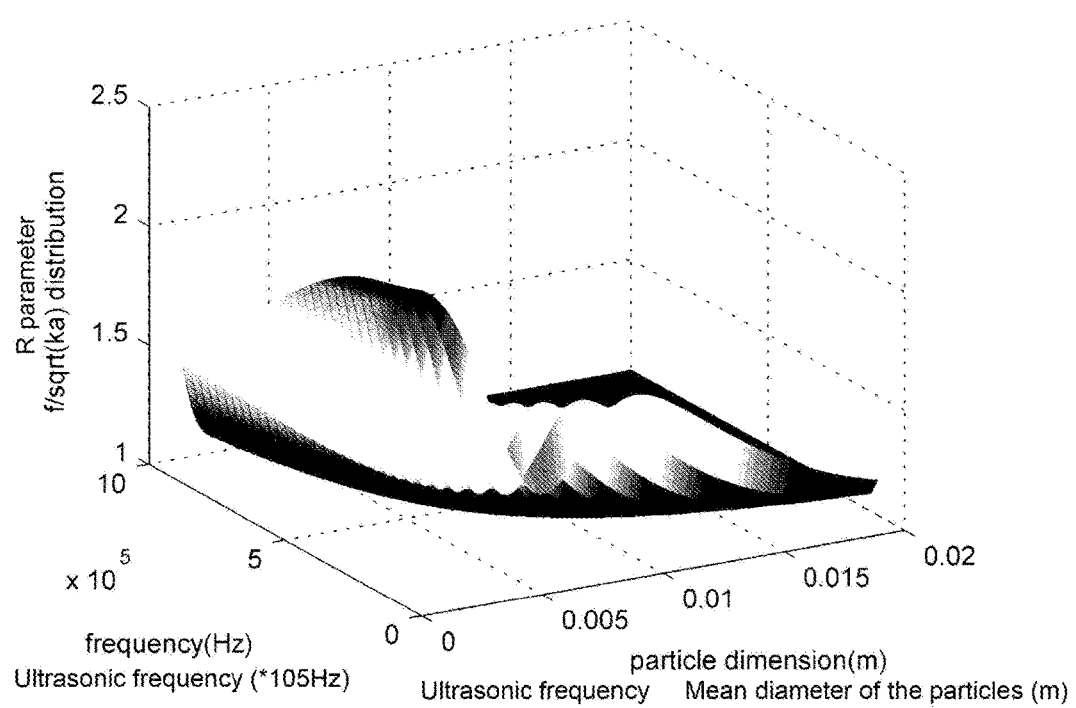
FIG. 3 is a graph showing an embodiment of a theoretical curve of the R parameter from the measurement method.

Referring to FIG. 3, FIG. 3 illustrates a theoretical curve of the R parameter of one embodiment. The particle density in the embodiment of FIG. 3 is 4,300 kg/m³, the mean diameter variance of the particles is 0.1 mm, while the velocity of the ultrasound in the fluid is 1,240 m/s. FIG. 3 shows the theoretical curve of the R parameter under this condition. The theoretical curve of the R parameter reflects the relationship between the R parameter and the mean diameter of the particles at different frequencies. The theoretical curve of the R parameter is changed when different particle density, mean diameter variance and velocity of the ultrasound in the fluid are set. According to practical application, different conditions are established to obtain the theoretical curve that is consistent with actual conditions.

Continuing to reference FIG. 2, in step 55, the mean diameter of the particles is determined from the theoretical value and theoretical curve of the R parameter.

The expression of the mean diameter of the particles $\langle a_s\rangle$ is shown in the following expression (5):

$$\langle a_s\rangle = \underset{\langle a_s\rangle}{\mathrm{argmax}}\sum_{i=1}^{n}(R_i - R_{theoretical,i})^2 \quad (5)$$

$R_i$ is the calculated value of the R parameter for the calculated i-th ultrasonic frequency $f_i$, $R_{theoretical,i}$ is the theoretical value of the R parameter for the i-th ultrasonic frequency $f_i$. The calculated value $R_i$ and theoretical curve of the R parameter are fitted to obtain the mean diameter of the particles. In one embodiment, the value of the mean diameter of the particles $a_s$ is found, such that the square and minimum of the difference between the plurality of the calculated values $R_i$ of the R parameter and the plurality of the theoretical value $R_{theoretical,i}$ of the R parameter under different frequencies can be calculated. In one embodiment, the ultrasonic frequency is a single frequency, where n=1. In this way, the mean diameter of the particles in a region can be obtained.

In step 56, the mass concentration M of the particles is determined from the mean diameter of the particles. The mass concentration M of the particles is calculated from the mean diameter of the particles $\langle a_s\rangle$ and parameter A. In this way, the mass concentration M of the particles in the corresponding regions can be obtained. The calculations of the measurement method 50 is simple and does not require iterations, while the parameters related to particle size and the parameters related to mass concentration can be calculated separately. Also, particles of a large size can be measured, and it is applicable to a wider range of particle sizes. As shown in FIG. 3, in this embodiment, the present method can measure particles having a mean diameter of 0.02 m. In addition, in some embodiments, the present method may also use one or more ultrasonic transducers of a single frequency to perform measurements of the mean diameter and mass concentration of the particles, facilitating practical applications and deployment.

Figure 4:
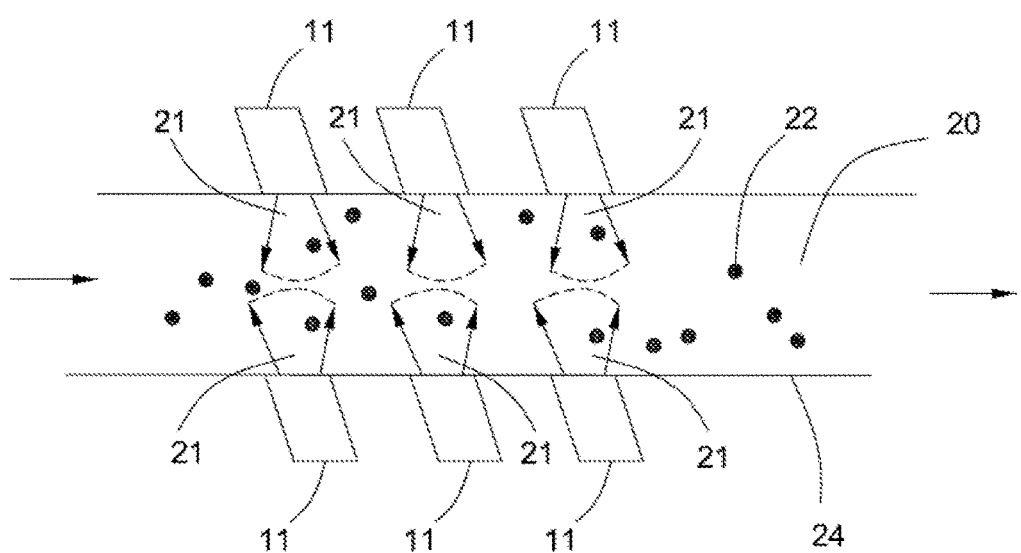
FIG. 4 shows a schematic view of a plurality of ultrasonic transducers mounted on a conduit.

In one embodiment, the measurement method 50 further comprises step 57 of determining the particle size distribution within the conduit region. In combination with referencing FIG. 4, a plurality of ultrasonic transducers 11 are arranged on the conduit 24 and spaced from each other, the ultrasonic transducers 11 transmit ultrasonic signals to a plurality of regions 21 of the fluid 20. In one embodiment, the plurality of ultrasonic transducers 11 are arranged and spaced along the longitudinal direction of the conduit 24. In another embodiment, the plurality of ultrasonic transducers 11 are arranged and spaced along the circumferential direction of the conduit 24. In yet another embodiment, the plurality of ultrasonic transducers 11 are arranged and spaced along the longitudinal direction and the circumferential direction of the conduit 24. The arrangement of the ultrasonic transducers 11 is not limited thereto and may be configured according to practical applications. Each of the ultrasonic transducers 11 may transmit ultrasonic signals covering a region 21 that approximates a cone. The regions covered by the plurality of ultrasonic transducers 11 do not overlap or partially overlap. In one embodiment, the same ultrasonic transducer 11 may transmit different frequencies. In another embodiment, different ultrasonic transducers 11 transmit different frequencies. According to steps 51-56, the mean diameter and mass concentration of the particles within each region are measured, and then the particle size distribution in the conduit regions is determined based on the mean diameter and the mass concentration of the particles in these regions. It is possible to determine the particle size distribution of the regions within the conduit covered by the plurality of ultrasonic transducers 11. In some embodiments, the particle size distribution within the entire conduit region can be measured.

In one embodiment, data of the particle size, mass concentration and/or particle size distribution may be displayed. In another embodiment, the particle size, mass concentration and/or particle size distribution may be used for other computational processing and/or control steps, for example, data of particles size, mass concentration and/or particle size distribution may be used to assist the flow rate calculation of the fluid, or to adjust the control of the drilling well system according to particle size, mass concentration and/or particle size distribution.

The operation of method 50 is illustrated in the form of a functional module, the sequence of the modules shown in FIG. 2 and the division of the operations in the modules are not limited to the illustrated embodiment. For example, some modules can be performed in a different order; operations in one module can be combined with operations in one or more other modules, or split into multiple modules. For example, the sequence of step 53 for calculating the calculated value of the R parameter and step 54 of determining the theoretical curve of the R parameter may be performed in reverse or simultaneously. The ultrasonic transducer 11 shown in FIG. 1 may be used to transmit ultrasonic signals and receive the return signals. The return signals may be processed by the ultrasonic transmitting and receiving devices 13, the digitizer 17 and the processor 19 in FIG. 1 to produce information on particle size, mass concentration and particle size distribution, to be displayed by the display 40. The processor 19 may be used to implement steps 53-57.

While the present invention has been described in detail with reference to specific embodiments thereof, it will be understood by those skilled in the art that many modifications and variations can be made in the present invention. It is, therefore, to be understood that the appended claims are intended to cover all such modifications and variations insofar as they are within the true spirit and scope of the invention.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:
   transmitting a plurality of ultrasonic signals to a fluid with particles;
   receiving a plurality of return signals reflected or backscattered from the particles;
   calculating one or more calculated values of a R parameter related to particle property of the particles according to the plurality of return signals;
   determining a theoretical curve of the R parameter;
   determining a mean diameter of the particles according to the one or more calculated values and the theoretical curve of the R parameter; and
   determining a mass concentration of the particles according the mean diameter.

2. The method of claim 1, further comprising:
   transmitting the plurality of ultrasonic signals to a plurality of regions in the fluid via a plurality of transducers arranging on a conduit and spaced from each other;
   determining the mean diameter and the mass concentration of the particles in each region; and
   determining a particle size distribution of the particles in the conduit according to the mean diameters and the mass concentrations of the particles in the plurality of regions.

3. The method of claim 1, wherein determining the mean diameter of the particles comprises fitting the one or more calculated values and the theoretical curve of the R parameter to get the mean diameter of the particles.

4. The measurement method according to claim 1, further comprising:
   determining a root-mean-square of voltage amplitudes of the return signals as a function of the particle property of the particles; and
   calculating the one or more calculated values according to the function.

5. The method of claim 1, wherein determining the theoretical curve of the R parameter comprises determining the theoretical curve according to an average backscatter form function and an average normalized total scattering cross-section.

6. A system, comprising:
   one or more transducers configured to transmit a plurality of ultrasonic signals to a fluid with particles and receive a plurality of return signals reflected or backscattered from the particles; and
   a processor coupled to the one or more transducers and configured to:
      calculate one or more calculated values of a R parameter related to particle property of the particles according to the plurality of return signals;
      determine a theoretical curve of the R parameter;
      determine a mean diameter of the particles according to the one or more calculated values and the theoretical curve of the R parameter; and
      determine a mass concentration of the particles according the mean diameter.

7. The system of claim 6, further comprising a conduit:
   wherein the one or more transducers comprise a plurality of transducers arranging on the conduit and spaced from each other to transmit the plurality of ultrasonic signals to a plurality of regions in the fluid; and
   wherein the processor is configured to:
      determine the mean diameter and the mass concentration of the particles in each region, and
      determine a particle size distribution of the particles in the conduit according to the mean diameters and the mass concentrations of the particles in the plurality of regions.

8. The system of claim 6, wherein the processor is configured to fit the one or more calculated values and the theoretical curve of the R parameter to get the mean diameter of the particles.

9. The system of claim 6, wherein the processor is configured to determine a root-mean-square of voltage amplitudes of the return signals as a function of the particle property of the particles; and calculate the one or more calculated values according to the function.

10. The system of claim 6, wherein the processor is configured to determine the theoretical curve according to an average backscatter form function and an average normalized total scattering cross-section.

* * * * *